United States Patent [19]

Cummings

[11] Patent Number: 4,843,867
[45] Date of Patent: Jul. 4, 1989

[54] SYSTEM FOR MONITORING STERILANT VAPOR CONCENTRATION

[75] Inventor: Arthur L. Cummings, Erie, Pa.

[73] Assignee: American Sterilizer Company, Erie, Pa.

[21] Appl. No.: 139,991

[22] Filed: Dec. 30, 1987

[51] Int. Cl.4 .................. G01N 37/00; B01D 3/42
[52] U.S. Cl. .......................... 73/23; 422/83; 422/98; 422/111; 374/28; 203/2; 203/3; 203/12; 203/DIG. 18
[58] Field of Search .......... 203/1, 91, 2, 3, 12, 203/DIG. 18; 422/27, 28, 111, 112, 83, 98; 364/413, 497, 499, 500, 501; 374/28; 73/336.5, 23

[56] References Cited

U.S. PATENT DOCUMENTS

| 2,369,900 | 2/1945 | Jennings et al. | 422/27 |
|---|---|---|---|
| 3,598,516 | 1/1969 | Shull et al. | 422/27 |
| 3,687,612 | 8/1972 | Ernst | 422/27 |
| 3,910,761 | 10/1975 | Hopkins | 422/108 |
| 4,066,399 | 1/1978 | Gunther | 422/27 |
| 4,067,691 | 1/1978 | McGady et al. | 422/1 |
| 4,169,123 | 9/1979 | Moore et al. | 422/29 |
| 4,169,124 | 9/1979 | Forstrom et al. | 422/33 |
| 4,261,950 | 4/1981 | Bainbridge et al. | 422/28 |
| 4,294,804 | 10/1981 | Baran | 422/27 |
| 4,309,381 | 1/1982 | Chamberlain et al. | 422/111 |
| 4,616,501 | 10/1986 | Mechlenburg | 73/24 |
| 4,637,916 | 1/1987 | Hennebert et al. | 422/27 |
| 4,642,165 | 2/1987 | Bier | 203/12 |

FOREIGN PATENT DOCUMENTS

| 8604698 | 8/1986 | PCT Int'l Appl. | 422/111 |
|---|---|---|---|
| 2052800 | 10/1980 | United Kingdom | 422/27 |

OTHER PUBLICATIONS

W. C. Schumb et al., "Hydrogen Peroxide" (Reinhold pub. 1955).
B. Lainer, "Humidity Sensors", Sensors (May 1986).
EG&G Environmental Equipment, Bulletins 3-100, 3-911, "Dew Tank Portable Humidity Meter", Model 911 Dew-All Digital Humidity Analyzer (publication dates unknown).
Panametrics brochures, "Moisture Measurement Systems", M-Series Probes and RH Series Relative Humidity Hygrometers (publication dates unknown).
General Eastern, "800-Series Polymer Type Relative Humidity Sensor" Kan. 1985, revised May 1985.

Primary Examiner—David L. Lacey
Assistant Examiner—V. Hanoharan
Attorney, Agent, or Firm—Kirkpatrick & Lockhart

[57] ABSTRACT

A system is provided for determining the concentration of a condensable vapor in the presence of at least one other condensable vapor, such as hydrogen peroxide and water vapors. The system includes generally a dew point sensor, a device for measuring at least one additional property of at least the other vapor such as relative humidity, and a microprocessor for fitting the dew point and additional property measurements into a modeled construct representative of the relationship between the vapors at a plurality of concentrations for each such vapor and at a plurality of corresponding dew point measurements. When used to determine the concentration of sterilant vapor in a sterilization system, the system also includes a sterilization chamber and an injector for injecting a measured quantity of the multicomponent condensable vapor into the chamber.

4 Claims, 1 Drawing Sheet

- □ — Water — 1.3 mg/L
- ○ — Water — 2.3 mg/L
- △ — Water — 3.5 mg/L
- ▽ — Water — 3.9 mg/L
- ◇ — Water — 4.6 mg/L
- ■ — Water — 5.5 mg/L

SYSTEM FOR MONITORING STERILANT VAPOR CONCENTRATION

BACKGROUND OF THE INVENTION

1. Field of the Invention

The present invention relates to systems for monitoring sterilant vapor concentration and more particularly, to a system for monitoring a condensable sterilant vapor in the presence of another condensable vapor.

2. Description of the Prior Art

In 1979 Moore et al. disclosed in U.S. Pat. No. 4,169,123 a method of sterilizing with hydrogen peroxide vapor. Forstrom et al. U.S. Pat. No. 4,169,124 disclosed a similar method wherein the concentration of the hydrogen peroxide vapor is less than 75 mg/L. Bier U.S. Pat. No. 4,642,165 discloses a method of vaporizing multicomponent liquids such as hydrogen peroxide and water, and passing the vapor into a sterilization chamber. Heretofore, no simple, unambiguous means of measuring hydrogen peroxide vapor concentration in the sterilization chamber has been available.

Hydrogen peroxide is rarely, if ever, used in a pure form. It is typically mixed with water. Hydrogen peroxide vapor, like water vapor, is a consensable gas, but is less volatile than water. When injected into a sterilizer along with water vapor, the hydrogen peroxide vapor may readily decompose into water and oxygen or condense into liquid. General physical properties, such as pressure, temperature and mass are therefore, not alone sufficient to provide an unambiguous measure of instantaneous hydrogen peroxide concentration in a sterilizer. Because of the potential for degradation of the sterilant, monitoring the hydrogen peroxide concentration is important to ascertain whether a sufficient sterilant concentration is maintained long enough to effect sterilization.

Known methods for determining hydrogen peroxide concentrations are not convenient for vapor phase hydrogen peroxide (VPHP) in a sterilizer because of sampling difficulties. Withdrawing a representative sample from a sterilizer is fraught with uncertainty because of the potential for degradation on surfaces (such as syringe needles), condensation, and, in the case of a vacuum sterilizer, because of a negative pressure gradient of up to 14 psi or more. A sample of vapor may be trapped in liquid water and subsequently analyzed for hydrogen peroxide by one of many known chemical or instrumental methods. Direct measurement of the VPHP may be accomplished by spectroscopic means with a very long (eg., 30 meters) cell and appropriate signal enhancement. Again, sampling the vapor is a problem. To overcome the vapor sampling difficulties, the spectroscopic cell might be mounted within the sterilizer chamber and means provided to transmit radiation through the chamber wall. These methods are cumbersome, expensive, and slow.

There is a need for a simple system to determine the vapor concentration of a condensable vapor of interest. There is a further need for a system to monitor sterilant vapor concentration. Finally, there is a further need for a system that will consistently provide such determinations quickly and accurately throughout the course of a sterilization cycle.

SUMMARY OF THE INVENTION

The present invention provides a system for monitoring the concentration of one vapor in a multicomponent vapor. The system will provide a determination of the concentration of at least one vapor component of the multicomponent condensable vapor. The multicomponent vapor is formed from component vapors comprising at least two condensable vapors. The system includes means for measuring a primary property of the multicomponent vapor, such as the dew point temperature, means for measuring at least one secondary property of at least one component of the multicomponent vapor, and means for fitting the primary and secondary property measurements into a modeled construct representative of the relationship between the component vapors at a plurality of concentrations of each such vapor component and at a plurality of primary property measurements correlating to such vapor component concentrations.

The second property measured could be, for example, (1) the relative humidity, (2) thermal conductivity, (3) total vapor pressure or (4) the mass of the injected multicomponent vapor and the volume of the area of interest.

The means for fitting the measurements into a modeled construct is preferably a microprocessor having means for storing the modeled construct and means for communicating data from the primary and secondary measuring means to the microprocessor.

In their preferred embodiment, the system monitors the concentration of a condensable sterilant vapor in a multicomponent vapor mixture where at least one other non-sterilant vapor is also condensable. Such a system would also include a sterilization chamber and means for injecting a predetermined quantity of the multicomponent vapor into the chamber.

BRIEF DESCRIPTION OF THE FIGURES

The present invention can be better understood by reference to the figures in which.

DETAILED DESCRIPTION OF THE PREFERRED EMBODIMENT

Figure 1:
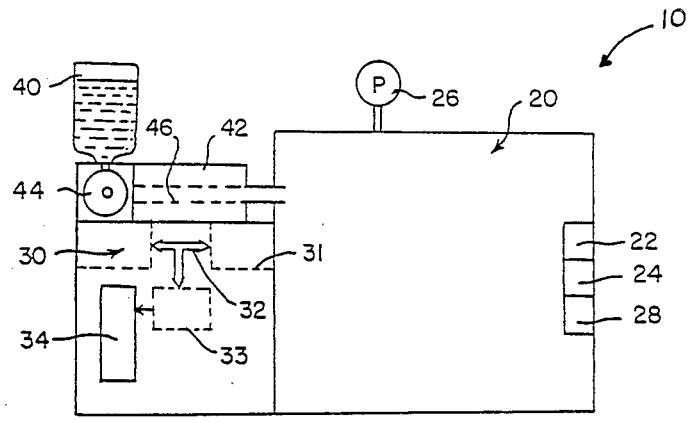
FIG. 1 is a diagram of the system of the present invention.

The principal components of the preferred embodiment of the system 10 of the present invention are illustrated in FIG. 1. The system includes a sterilization chamber 20, a microprocessor 30 having an input interface 31 for communicating data to the microprocessor 30 via a data but 32. The microprocessor 30 outputs data at a data display 34 through the data bus 32 and an output interface 33. The system also includes a source 40 of a multicomponent liquid, a vaporizer 42 for vaporizing the multicomponent liquid into a multicomponent vapor, an injection valve 44 for injecting the liquid into the vaporizer 42 for passage of the vapor into the sterilization chamber 20, a dew point sensor 22 and an additional sensor 24 for measuring a secondary property of one of the components of the multicomponent vapor. A pressure gauge 26 and thermometer 28 should also be provided.

The sterilization chamber 20 may be any suitable known chamber and need not be a pressure/vacuum vessel. Any closed (or closable) space having a defined volume which is compatible with the particular sterilant vapor will suffice. For example, the chamber 20 may be a clean room, a glove box, an incubator, or any more conventional sterilizer equipped for vapor sterilization.

Microprocessor 30, input interface 31 and output interface 33 may similarly be any suitable known components or computer system which includes means for receiving, storing and analyzing data for reporting such data and the results of such analyses.

Vaporizer 42 should be constructed of materials which are compatible to the components of the multi-component liquid/vapor. For example, if the vapor is a hydrogen peroxide/water mixture, then vaporizer 42 may be contructed of passivated stainless steel, aluminum or alloys or aluminum which are compatible to hydrogen peroxide. The vaporizer 42 must have a heated surface 46 structured to ensure contact with the injection liquid to vaporize it for passage into chamber 20. The heated surface 46 may be heated by any suitable known means.

Injector 44 may be any suitable valve, such as a three-way ball valve, which can be inject predetermined quantities of the multicomponent liquid into the vaporizer 42 at the desired time and rate.

Broadly, the invention pertains to the monitoring of one condensable vapor in the presence of at least one other condensable vapor. The system of the invention utilizes the measurement of a primary property of the combined vapors and the measurement of at least one secondry property of the vapor, or one of them, to determine therefrom the concentration of the sterilant vapor.

The primary property is preferably more strongly dependent on the concentration of the vapor of interest than on the other vapor. The dew point temperature or saturated level is an example of a suitable primary property. The secondary property may be specific to the other component of the multicomponent vapor, equi-sensitive to both the components of the vapor, or unequally sensitive to both. Pressure, mass and thermal conductivity are essentially equi-sensitive properties which are suitable as secondary properties in the system of the present invention. Humidity is an example of a secondary property which is specific to water vapor, the non-sterilant vapor component of the preferred embodiment of the multicomponent vapor.

For purposes of the detailed description, the system for monitoring the concentration of a sterilant vapor will be described by reference to such a system wherein a binary compoisition of hydrogen peroxide ($H_2O_2$) vapor as a sterilant vapor of interest and water ($H_2O$) vapor as the other, non-sterilant vapor is used. Those skilled in the art will appreciate that the monitoring system disclosed herein can be adapted for use with other multicomponent vapors comprised of two or more condensable vapors.

Dew point is the saturation temperature of a given concentration of condensable vapors. A decrease of the temperature of the gas below the dew point results in condensation of some of the vapor to liquid. Heating the vapor above the dew point may not change the vapor concentration significantly, but does increase the saturation level. The heated vapor is thus, no longer saturated. A higher concentration of gas will have a higher dew point.

Dew point has been used to determine water vapor concentration in a single vapor system. When a multi-component vapor is present, dew point alone provides an ambiguous measure of the vapor mixture. Hydrogen peroxide and water vapors are known to co-condense. The concentration of one, particularly in a closed system, affects the saturation level of the other. For example, referring to FIG. 2, there is a smooth relationship between hydrogen peroxide vapor concentration and dew point as long as the water vapor concentration remains constant. When the water vapor concentration changes, however, the relationship between the hydrogen peroxide concentration and dew point changes also. The problem is compounded in sterilization systems because hydrogen peroxide vapor can decompose into water vapor. Thus, the relative concentrations of the two vapors are subject to constant change. Dew point measurements, therefore, or any similar composite property of water and hydrogen peroxide vapors are not a readily apparent means of measuring hydrogen peroxide vapor concentrations.

However, when the admittedly ambiguous and unstable dew point measurement is combined with the measurement of a secondary property, such as the relative humidity of the water vapor, then the water vapor concentration can be determined. Knowledge of the water vapor concentration can be used to deduce the instantaneous hydrogen peroxide concentration from the dew point measurements. Note from FIG. 2, for example, that in the area of the graph near 18° C. dew point and 1.1 mg/L hydrogen peroxide concentration, the dew point changes 0.8° C. for a 0.1 mg/L change in hydrogen peroxide concentration, but varies only 0.2° C. for a similar change in water vapor concentration. On a mass basis, the dew point is about four times as sensitive to hydrogen peroxide vapor as to water vapor. On a molecular basis, the factor is eight. Thus, variations in hydrogen peroxide concentration can be sensitively detected by dew point measurements.

The preferred embodiment of the system of the present invention utilizes the relationship between the hydrogen peroxide vapor concentration, the water vapor concentration and the dew point to provide a simple and accurate system for monitoring sterilant vapor concentration throughout a sterilization cycle.

Microprocessor 30 is used to store a modeled construct of the aforementioned relationship. Input interface 31 communicates data generated by dew point sensor 22, secondary property sensor 24, pressure gauge 26 and thermometer 28 via data bus 32 in a known manner. The microprocessor must be programmed by suitable known means to convert the relative humidity measurement to a corresponding water vapor concentration which is then fit, along with the dew point measurement into the stored construct for comparison. The corresponding hydrogen peroxide concentration is then displayed on display 34.

The modeled construct is developed according to the method set forth below. The calculations are based on known properties of hydrogen peroxide and water mixtures[1]. Table I sets forth the total vapor pressure over a liquid solution of hydrogen peroxide and water.

[1] W. C. Schumb et al. "Hydrogen Peroxide", pp. 221–227 (Reinhold pub. 1955).

TABLE 1

Total Vapor Pressure (mm. Hg) of Hydrogen Peroxide - Water Solutions

| Temp. (°C.) | Mole Fraction of Hydrogen Peroxide in Liquid | | | | | | | | | | |
|---|---|---|---|---|---|---|---|---|---|---|---|
| | 0 | 0.1 | 0.2 | 0.3 | 0.4 | 0.5 | 0.6 | 0.7 | 0.8 | 0.9 | 1.0 |
| 0 | 4.58 | 4.06 | 3.45 | 2.81 | 2.20 | 1.66 | 1.21 | 0.856 | 0.593 | 0.404 | 0.272 |
| 10 | 9.20 | 8.17 | 6.96 | 5.70 | 4.49 | 3.42 | 2.53 | 1.83 | 1.30 | 0.915 | 0.642 |
| 20 | 17.5 | 15.6 | 13.3 | 10.9 | 8.69 | 6.68 | 5.00 | 3.66 | 2.64 | 1.89 | 1.36 |
| 25 | 23.7 | 21.1 | 18.1 | 14.9 | 11.9 | 9.17 | 6.90 | 5.09 | 3.71 | 2.69 | 1.95 |
| 30 | 31.8 | 28.3 | 24.3 | 20.1 | 16.0 | 12.4 | 9.41 | 6.99 | 5.14 | 3.77 | 2.77 |
| 40 | 55.3 | 49.3 | 42.4 | 35.2 | 28.3 | 22.2 | 17.0 | 12.8 | 9.55 | 7.14 | 5.36 |
| 50 | 92.6 | 82.5 | 71.1 | 59.3 | 48.1 | 37.9 | 29.3 | 22.4 | 17.0 | 12.9 | 9.90 |
| 60 | 149 | 133 | 115 | 96.6 | 78.7 | 62.6 | 49.0 | 37.8 | 29.1 | 22.5 | 17.5 |
| 70 | 234 | 209 | 181 | 152 | 125 | 100 | 79.0 | 61.8 | 48.2 | 37.8 | 20.8 |
| 80 | 355 | 318 | 216 | 233 | 192 | 155 | 124 | 97.8 | 77.2 | 61.3 | 49.1 |
| 90 | 520 | 471 | 410 | 348 | 289 | 235 | 189 | 150 | 120 | 96.5 | 78.2 |
| 100 | 760 | 682 | 595 | 507 | 422 | 346 | 280 | 226 | 182 | 148 | 121 |
| 110 | 1074 | 965 | 845 | 722 | 605 | 499 | 407 | 331 | 269 | 221 | 182 |
| 120 | 1489 | 1339 | 1175 | 1008 | 848 | 704 | 578 | 474 | 389 | 322 | 269 |
| 130 | 2025 | 1824 | 1604 | 1381 | 1168 | 974 | 807 | 666 | 552 | 460 | 387 |
| 140 | 2709 | 2443 | 2153 | 1860 | 1580 | 1326 | 1105 | 919 | 767 | 645 | 546 |
| 150 | 3568 | 3222 | 2847 | 2467 | 2105 | 1776 | 1489 | 1247 | 1048 | 887 | 755 |

Table II sets forth the vapor composition over a liquid solution of hydrogen peroxide and water in a closed system.

TABLE II

Vapor Composition (Mole Fraction $H_2O_2$), Over Hydrogen Peroxide - Water Solutions

| Temp. (°C.) | Mole Fraction Hydrogen Peroxide in Liquid | | | | | | | | |
|---|---|---|---|---|---|---|---|---|---|
| | 0.1 | 0.2 | 0.3 | 0.4 | 0.5 | 0.6 | 0.7 | 0.8 | 0.9 |
| 0 | 0.002 | 0.006 | 0.015 | 0.031 | 0.060 | 0.112 | 0.202 | 0.352 | 0.600 |
| 10 | 0.003 | 0.008 | 0.018 | 0.037 | 0.070 | 0.128 | 0.224 | 0.381 | 0.626 |
| 20 | 0.003 | 0.009 | 0.020 | 0.041 | 0.077 | 0.138 | 0.238 | 0.397 | 0.640 |
| 25 | 0.003 | 0.010 | 0.022 | 0.044 | 0.081 | 0.144 | 0.247 | 0.407 | 0.648 |
| 30 | 0.003 | 0.010 | 0.023 | 0.046 | 0.083 | 0.151 | 0.255 | 0.417 | 0.656 |
| 40 | 0.004 | 0.012 | 0.026 | 0.052 | 0.094 | 0.163 | 0.272 | 0.435 | 0.671 |
| 50 | 0.005 | 0.014 | 0.030 | 0.057 | 0.103 | 0.175 | 0.287 | 0.452 | 0.684 |
| 60 | 0.005 | 0.015 | 0.033 | 0.063 | 0.111 | 0.187 | 0.302 | 0.468 | 0.696 |
| 70 | 0.006 | 0.017 | 0.036 | 0.068 | 0.120 | 0.199 | 0.316 | 0.482 | 0.707 |
| 80 | 0.007 | 0.019 | 0.040 | 0.074 | 0.128 | 0.210 | 0.329 | 0.495 | 0.716 |
| 90 | 0.007 | 0.021 | 0.043 | 0.080 | 0.136 | 0.221 | 0.342 | 0.508 | 0.725 |
| 100 | 0.008 | 0.023 | 0.047 | 0.085 | 0.144 | 0.231 | 0.354 | 0.519 | 0.733 |
| 110 | 0.009 | 0.025 | 0.051 | 0.091 | 0.152 | 0.241 | 0.365 | 0.530 | 0.740 |
| 120 | 0.010 | 0.027 | 0.054 | 0.097 | 0.160 | 0.251 | 0.376 | 0.540 | 0.747 |
| 130 | 0.011 | 0.029 | 0.058 | 0.102 | 0.168 | 0.260 | 0.386 | 0.549 | 0.753 |
| 140 | 0.012 | 0.031 | 0.061 | 0.108 | 0.175 | 0.269 | 0.396 | 0.558 | 0.758 |
| 150 | 0.013 | 0.033 | 0.065 | 0.113 | 0.182 | 0.278 | 0.405 | 0.566 | 0.763 |

The vapor concentrations at saturation temperatures (dew point) can be determined by combining vapor composition data from Table II with vapor pressure data from Table I. For example, referring to Table II, at 20° C., a saturated vapor composed of 0.138 1 mole fraction hydrogen peroxide (and thus, 0.862 mole fraction water) is in equilibrium with its liquid counterpart composed of 0.6 mole fraction hydrogen peroxide (and 0.4 mole fraction water). Referring to Table I, at 20° C., the vapor pressure over a solution composed of 0.6 mole fraction hydrogen peroxide (and 0.4 mole fraction water) is 5.00 mm Hg.

The ideal gas law ($PV = nRT$) together with the respective molecular weights of the vapors can now be used to calculate the concentration of each component in the multicomponent vapor mixture according to the following relationships:

$C = w/V = Mn/V = Mp/RT$ where $C$ = the concentration of vapor, eg., mg/L
w = mass
V = Volume
M = molecular weight
n = moles of vapor
p = partial pressure of vapor
R = universal gas constant, and
T = temperature of vapor (and liquid);
and $p = YP$
where Y = vapor mole fraction, and
P = total vapor pressure.

In the example expressed above, at 20° C. the saturated hydrogen peroxide vapor concentration is determined by the relationship $MYP/RT$, or $$\frac{(34.02 \text{ g/mole}) (0.138) (5.00 \text{ mm Hg})}{(760 \text{ mm Hg/atm}) \left( 0.082 \frac{\text{liter} - \text{atm}}{\text{mole} - °K.} \right)(293° K.)} =$$

0.00128 g/L

The saturated water vapor concentration is similarly determined.

$$\frac{(18.02 \text{ g/mole}) (0.862) (5.00 \text{ mm Hg})}{(760 \text{ mm Hg/atm}) \left( 0.082 \frac{\text{liter} - \text{atm}}{\text{mole} - °K.} \right)(293° K.)} =$$

0.00425 g/L

Thus, a vapor mixture comprises of 1.3 mg hydrogen peroxide per liter and 4.2 mg water per liter has a dew point of 20° C. This point is indicated by a dot in a circle, in FIG. 2. Other examples, typical of sterilization conditions, are summarized in Table III.

TABLE III

Selected Dew Point and Vapor Composition Examples

| Dewpoint °C. | $H_2O_2$ Vapor | | Water Vapor | | Total Vapor Pressure mm Hg |
|---|---|---|---|---|---|
| | Mole Fraction | mg/L | Mole Fraction | mg/L | |
| 1 | 0.12 | 0.3 | 0.88 | 1.3 | 1.4 |
| 4 | 0.01 | 0.09 | 0.99 | 4.6 | 4.5 |
| 4 | 0.18 | 0.5 | 0.82 | 1.2 | 1.4 |
| 4 | 0.35 | 0.6 | 0.65 | 0.6 | 0.9 |
| 10 | 0.18 | 0.7 | 0.82 | 1.8 | 2.1 |
| 20 | 0.14 | 1.3 | 0.86 | 4.2 | 5.0 |
| 20 | 0.22 | 1.6 | 0.78 | 3.0 | 4.6 |
| 80 | 0.03 | 10.7 | 0.97 | 203.2 | 256.0 |
| 80 | 0.18 | 38.0 | 0.82 | 88.0 | 131.0 |

To complete the modeled construct, the calculations can be repeated for many combinations of temperature, water vapor concentration and hydrogen peroxide vapor concentration. As can be observed, the variables in the above exemplary calculations are the mole fractions of the water and hydrogen peroxide vapors, the total pressure of the two vapors and the temperature. The molecular weights of the vapor components for a particular multicomponent vapor, the universal gas constant, 0.082 liter-atm/mole-°K., and the conversion factor, 760 mm Hg/atm are known.

For conditions which do not specifically appear in Tables I and II, one may interpolate between entries. Alternatively, equations may be used, which describe the vapor pressure and composition over liquid solutions of the components of interest. For hydrogen peroxide and water mixtures, such equations, based on experimental data, are available in the known literature, for example, in Schumb, et al. pp. 225-227 referenced in footnote 1 above.

The modeled construct can be used to calculate concentrations of the vapor components from measurements of physical properties of the vapor.

Figure 2:
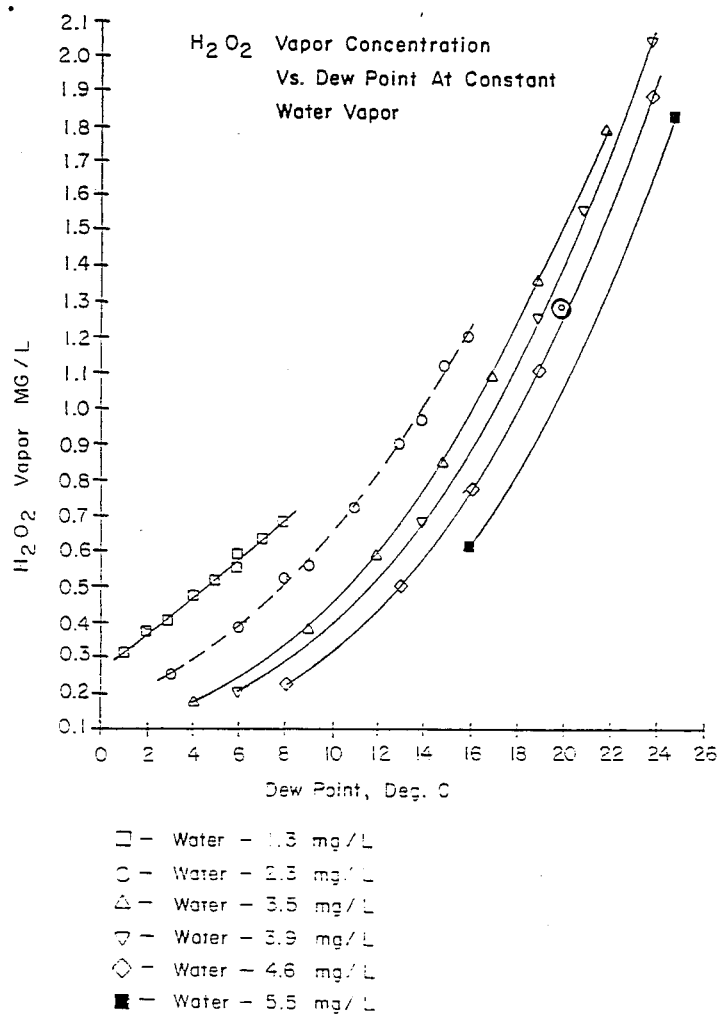
FIG. 2 is a graph of predetermined information concerning the relationship between hydrogen peroxide concentration, water concentration and the corresponding dew point temperature.

The measurement of dew point alone, as stated above, is not sufficient to unambiguously determine the hydrogen peroxide vapor concentration. However, humidity measurements provide sufficient information, when combined with dew point temperature, to specify the hydrogen peroxide vapor concentration. Absolute humidity data (water per unit volume) is required for the calculations. A relative humidity sensor 24 can be used and, by known relationships between relative humidity, vapor temperature and absolute humidity as set forth below, the water vapor concentration can be determined.

$$RH = 100\% * c/c0$$

where
  $RH$ = relative humidity, %
  $c$ = concentration of water vapor, eg., mg/L
  $c0$ = concentration of water vapor is saturated The absolute humidity, c, is calculated from a relative humidity measurement by multiplying relative humidity, RH, by c0/100. The saturation level, c0, is know to be related exponentially to temperature. For example, $$c0 = e^{[f-g/T]}$$

where
  $e$ = the natural base, 2.718
  $f$ = constant = 19.89 for T = 278 to 323
  $g$ = constant = 4993 for T = 278 to 323
  $T$ = temperature, degrees Kelvin For example, referring to FIG. 2, if a dew point of 14° C. obtained from dew point sensor 22 and an independent humidity measurement obtained from a humidity sensor 24 indicating that the water vapor concentration was 3.9 mg/L, are communicated by suitable known means to microprocessor 30 and compared to the stored modeled construct, represented by FIG. 2, the corresponding hydrogen peroxide vapor concentration, which must be 0.69 mg/L, would be shown on display 34. As the sterilization cycle progresses, the humidity and dew points will change. The new data would be communicated to microprocessor 30 and the corresponding instantaneous hydrogen peroxide vapor concentration would be displayed.

Display 34 may be equipped with a suitable recording device to record the changing concentrations to provide a permanent record of the sterilant vapor concentration throughout the sterilization cycle.

The general method of calculating hydrogen peroxide vapor concentration from measurement of two properties requires knowledge (e.g., through prior calibration) of the functional dependence of the properties on the concentrations of hydrogen peroxide, water, and any other sensible conditions. The measured responses to mixtures of unknown composition can be used in simultaneous solution of the response functions to provide quantitation of hydrogen peroxide and water vapor concentrations.

For example, suppose the response functions of sensor Y and sensor Z are both linear, e.g., $$Y = a0 + a1*[H] + a2*[W]$$

$$Z = b0 + b1*[H] + b2*[W]$$

where
  Y = magnitude of response of sensor Y
  Z = magnitude of response of sensor Z
  a0, a1, a2 = constants determined by calibration
  b0, b1, b2 = constants detrmined by calibration
  [H] = concentration of hydrogen peroxide vapor
  [W] = concentration of water vapor Simultaneous solution of these equations for [H] and [W] yields:

$$[H] = [a2*(Z-b0) - b2*(Y-a0)]/(a2*b1 - b2*a1)$$

$$[W] = (Y - a0 - a1*[H])/a2$$

For example, mass and pressure are linear functions of vapor concentrations. The concentration of each component of a two-component vapor can be calculated from measurements of the mass of liquid vaporized into a known volume and the associated pressure rise. Let Y be the mass injected, in grams, and Z be the pressure rise, in mm Hg. If the sterilizer volume is 50 L and the temperature is 55° C., then

| a0 = 0    | b0 = 0     |
|-----------|------------|
| a1 = 0.05 | b1 = 0.601 |
| a2 = 0.05 | b2 = 1.134 | and the following concentrations would result from application of the equations to the following measurements of Y and Z:

| Y grams | Z mm Hg | [H] mg/L | [W] mg/L |
|---------|---------|----------|----------|
| 0.5     | 9.74    | 3.00     | 7.00     |
| 1.0     | 19.48   | 6.00     | 14.00    |
| 1.83    | 35.66   | 10.96    | 25.63    |
| 1.83    | 38.00   | 6.57     | 30.02    |

Total vapor concentration may also be determined directly from measurement of the mass of liquid vaporized into a chamber of known volume. Pressure measurements can also provide total vapor concentration in vacuum conditions, where the water and hydrogen peroxide vapor constitute a signficant portion of total pressure. Thermal conductivity measurements relate to total vapor concentration if thermal conditions and background gas concentrations are stable. Thus, the secondary property measured need not be relative humidity. Sensor 24 can be a thermal conductivity sensor or a pressure gauge.

Dew point sensors which measure the temperature of condensate formation are commercially available. Relative humidity sensors, thermal conductivity sensors and pressure gauges are also commercially available.

Predetermined calculations according to the previously described methods can be made for a wide range of hydrogen peroxide vapor concentrations, water vapor concentrations, dew point temperatures, vapor temperatures and relative humidity values to develop the modeled construct for use within a particular sterilization system. The modeled construct can then be stored by suitable known means in a microprocessor for use in conjunction with subsequent sterilization cycles to monitor hydrogen peroxide vapor concentrations throughout such sterilization cycles.

What is claimed is:

1. A system for monitoring the concentration of a first vapor in the presence of at least one other vapor comprising:
    a chamber;
    means for injecting a predetermined quantity of a multicomponent vapor into said chamber, wherein said multicomponent vapor is formed from component vapors comprising a condensable first vapor and at least one other condensable vapor;
    means for measuring a primary property of said multicomponent vapor;
    means for measuring a secondary property of at least one component of said multicomponent vapor; and
    means for fitting said primary and secondary property measurements into a modeled construct representative of the relationship between said first vapor and said at least one other vapor at a plurality of concentrations of each said component vapor and at a plurality of said primary property measurements correlating to each said component vapor concentration.

2. The system of claim 1 wherein said first vapor is hydrogen peroxide vapor, said other vapor is water vapor, said means for measuring a primary property is a dew point sensor and said means for measuring a secondary property is a relative humidity sensor.

3. The system of claim 1 wherein said means for measuring said secondary property is a thermal conductivity sensor.

4. The system of claim 1 wherein said means for fitting measurements is a microprocessor having means for storing said modeled construct and means for communicating data from said primary property measuring means and said secondary property measuring means to said microprocessor.

* * * * *

UNITED STATES PATENT AND TRADEMARK OFFICE
CERTIFICATE OF CORRECTION

PATENT NO. : 4,843,867

DATED : July 4, 1989

INVENTOR(S) : Arthur L. Cummings

It is certified that error appears in the above-identified patent and that said Letters Patent is hereby corrected as shown below:

Title page:

IN OTHER PUBLICATIONS, delete "Kan." and substitute therefor -- Jan.--.

Col. 2, line 53, delete "but" and substitute therefor -- bus--.

Col. 3, line 18, delete "injection" and substitute therefor --injected--.

Col. 3, line 31, delete "secondry" and substitute therefor --secondary--.

Col. 3, line 52, delete "compoisition" and substitute therefor --composition--.

Col. 8, line 24, delete "detrmined" and substitute therefor --determined--.

Signed and Sealed this

Third Day of April, 1990

Attest:

HARRY F. MANBECK, JR.

*Attesting Officer*    *Commissioner of Patents and Trademarks*